US006392127B1

(12) United States Patent
Charne et al.

(10) Patent No.: US 6,392,127 B1
(45) Date of Patent: *May 21, 2002

(54) OILSEED BRASSICA CONTAINING AN IMPROVED FERTILITY RESTORER GENE FOR OGURA CYTOPLASMIC MALE STERILITY

(75) Inventors: David G. Charne, Guelph; Ian Grant, Orton, both of (CA); Konrad Kraling, Schwedeneck (DE); Jayantilal D. Patel, Thornhill (CA); Jean-Claude M. Pruvot, Blois (FR); Lomas K. Tulsieram, Mississauga (CA)

(73) Assignee: Pioneer Hi-Bred International, Inc., Des Moines, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,296
(22) PCT Filed: Dec. 19, 1997
(86) PCT No.: PCT/CA97/01005
  § 371 Date: Feb. 10, 1999
  § 102(e) Date: Feb. 10, 1999
(87) PCT Pub. No.: WO98/27806
  PCT Pub. Date: Jul. 2, 1998

(30) Foreign Application Priority Data

Dec. 24, 1996 (CA) ............................................. 2193938
Aug. 26, 1997 (EP) ............................................. 97306490

(51) Int. Cl.[7] .......................... A01H 1/02; A01H 1/00; A01H 1/04; A01H 5/00; A01H 5/10
(52) U.S. Cl. .................... 800/306; 800/260; 800/264; 800/271; 800/274; 800/303
(58) Field of Search ............................... 800/303, 306, 800/260, 264, 271, 274

(56) References Cited

U.S. PATENT DOCUMENTS

| | | | |
|---|---|---|---|
| 4,658,085 A | 4/1987 | Beversdorf et al. | 800/1 |
| 4,751,347 A | 6/1988 | Erickson | 800/1 |
| 5,750,827 A | * 5/1998 | Debonte et al. | 800/200 |
| 5,789,566 A | 8/1998 | Bonhomme et al. | 536/23.6 |
| 5,973,233 A | * 10/1999 | Burns et al. | 800/306 |
| 6,229,072 B1 | 5/2001 | Burns et al. | 800/306 |

FOREIGN PATENT DOCUMENTS

| | | | |
|---|---|---|---|
| EP | 0599042 | 6/1994 | A01H/1/02 |
| EP | 0 599 042 A1 | 6/1994 | A01H/1/02 |
| EP | 0 599 042 A * | 6/1994 | A01H/1/02 |
| EP | 0 671 121 A1 | 9/1995 | A01H/1/02 |
| EP | 0671121 | 9/1995 | A01H/1/02 |
| WO | WO 93/06714 | 4/1993 | A01H/1/02 |
| WO | WO 9306714 | 4/1993 | A01H/5/10 |
| WO | WO 97/02737 | 1/1997 | A01H/1/04 |
| WO | WO 9702737 | 10/1997 | A01H/1/04 |

OTHER PUBLICATIONS

Daun et al. Journal of the American Oil Chemists Society, vol. 65, pp. 122–126, 1988.*

Jain et al. Current Science, vol. 58, pp.1 76–180, 1989.*

Sang et al., "Glucosinolate Profiles in the Seed, Root and Leaf Tissue of Cabbage, Mustard, Rapeseed, Radish and Swede", Can. J. Plant Sci. 64:77–93 (1984).

Pellan–Delourme et al., "Cytoplasmic male sterility in rapeseed (Brassica napus L): female fertility of restored rapeseed with "Ogura" and cybrids cytoplasma", Genome, 30:234–238 (1988).

Love et al., "Development of Low Glucosinolate Mustard", Can. J. Plant Sci., 70:419–424 (1990).

Renard et al., "Production of F1 Hybrid Seeds Using a Cytoplasmic Male Sterility", C.R. Acad. Agric, Fr., 77:49–58 (1991) (Abstract only).

Daun et al., Use of Gas Liquid Chromatography for Monitoring the Fatty Acid Composition of Canadian Rapeseed [1,2], J. Am. Oil Chem. Soc., 60(1):1751–1754 (1983).

Delourme et al., "Breeding Double Low Restorer Lines in Radish Cytoplasmic Male Sterility of Rapeseed (Brassica Napus L.)", Proc. p[th] Int. Rapeseed Conf., Cambridge, England, pp. 6–8 (1995).

Delourme et al., "Radish Cytoplasmic Male Sterility in Rapeseed: Breeding Restorer Lines with a Good Female Fertility", Proc 8th Int. Rapeseed Conf., Saskatoon, Canada, pp. 1506–1510 (1991).

Delourme et al., "Identification of RAPD markers linked to a fertility restorer gene for the Ogura radish cytoplasmic male sterility of rapeseed (Brassica napus L)", Theor Appl Genet, 88:741–748 (1994).

Delourme et al., "Linkage between an isozyme marker and a restorer gene in radish cytoplasmic male sterility of rapeseed (Brassica napus L.)", Theor Appl Genet, 85:222–228 (1992).

(List continued on next page.)

Primary Examiner—David T. Fox
(74) Attorney, Agent, or Firm—Pioneer Hi-Bred International, Inc.

(57) ABSTRACT

The invention is a Brassica plant comprising a homozygous fertility restorer gene for ogura cytoplasmic male sterility, in addition to oilseed, meal and oil produced from the plant, and the use of oilseed of the plant for preparing oil and/or meal. Upon pollination, the plant yields oilseeds having a total glucosinolate content of not more than 30 μmol/gram, not more than 25 μmol/gram or not more than 20 μmol/gram and, optionally, an erucic acid content of no more than two percent by weight based upon the total fatty acid content. The Brassica plant may be Brassica napus, Brassica campestris, or Brassica juncea.

33 Claims, 5 Drawing Sheets

OTHER PUBLICATIONS

International Standard ISO 9167–1:1992(E), "Rapeseed—Determination of glucosinolates content—Part 1: Method using high–performance liquid chromatography".

Paul et al., "Inheritance of S–methyl–L–cysteine sulphoxide and thiocyanate contents inforage rape (*Brassica napus* L.)", *Theor Appl Genet*, 72:706–709 (1986).

Pellan–Delourme et al., "Male Fertility Restoration in *Brassica napus* with Radish Cytoplasmic Male Sterlity", Proc. 7th Int. Rapeseed Conf., Poznan, Poland, p. 199–203 (1987).

Pellan–Delourme et al., "Cytoplasmic male sterility in rapeseed (*Brassica napus* L): female fertility of restored rapeseed with "Ogra" and cybrids cytoplasms" *Genome*, 30:234–238 (1988).

Pelletier et al., "Molecular, Phenotypic and Genetic Characterization of Mitochondrial Recombinants in rapeseed", Proc. 7th Int. Rapeseed Conf., Poznan, Poland, pp. 113–118 (1987).

Rakow et al., "Opportunities and Problems in Modification of Levels of Rapeseed $C_{18}$ Unsaturated Fatty Acids[1]", *J. Am. Oil Chem. Soc.*, 50(10):400–403 (1973).

Ratledge et al., "Biotechnology for the Oils and Fats Industry", *Am. Oil Chemists' Society*, Champaign, pp.328.

Robbelen, Gerhard, Changes and Limitations of Breeding for Improved Polyenoic Fatty Acids in Rapeseed *Brassica napus* L., Z. Pflanzenzüchtg, 75:93–105 (1975).

Sosulski et al., "Determination of Glucosionolates in Canola Meal and Protein Products by Desulfation and Capillary Gas–Liquid Chromatography", *J. Agric. Food Chem.*, 32:1172–1175 (1984).

Stefannsson, B.R., "The Development of Improved Rapeseed Cultivars" in High and Low Erucic_acid Rapeseed Oils, edited by J. Kramer, F. Sauer, W. Pigden, Academic Press Canada, Toronto, Chapter 6, pp. 143–159 (1983).

U.S Ser. No. 4,751,347, Erickson, filed 1986.

U.S. Ser. No. 4,658,085, Beversdorf et al., filed 1985.

Pellan–Delourme, R. and Renard, M. "Cytoplasmic male sterility in rapeseed (*Brassica napus* L.): female fertility of restored rapeseed with 'Ogura 'and cybrids cytoplasms" (1988) Genome, 30:234–238.

Love, H.K., et al. "Development of Low Glucosinolate Mustard" (Apr. 1990)Can J. Plant Sci. 70:419–424.

Renard, M. et al. "Production of F1 Hybrid Seeds Using a Cytoplasmic Male Sterility" (1991) C.R. Acad Agric. 77:49–58, Abstract only.

J. K. Daun, et al., *J. Amer. Oil Chem. Soc.*, 60:1751–1754 (1983).

Delourme, R., F. Eber, M. Renard, "Breeding Double Low Restorer Lines in Radish Cytoplasmic Male Sterility of Rapeseed (*Brassica napus* L.")", Proc. 9th Int. Rapeseed Conf., Cambridge, England (1995), p. 6–8.

Delourme, R., F. Eber, M. Renard, " Radish Cytoplasmic Male Sterility in Rapeseed: Breeding Restorer Lines With a Good Female Fertility", Proc. 8th Int. Rapeseed Conf., Saskatoon Canada, 1506–1510 (1991).

Delouorme, R., A. Bouchereau, N. Hubert, M. Renard, B.S. Landry," Identification of RAPD Markers Linked to a Fertility Restorer Gene for the Ogura Radish Cytoplasmic Male Sterility of Rapeseed (*Brassica napus* L.)", *Theor. Appl. Gener.* 88:741–748 (1994).

Delourme, R. and F. Eber., " Linkage Between An Isozyme Marker and a Restorer Gene in Radish Cytoplasmic Male Sterility of Rapeseed (*Brassica napus* L."), *Theor. Appl. Genet.*, 85:222–228 (1992).

International Standard ISO 9167–1:1992(3), "Rapeseed—Determination of Glucosinolates Content—Part 1: Method Using High–Performance Liquid Chromatography."

Paul, et al., "Inheritance of S–methyl–L–cysteine Sulphoxide and Thiocyanate Contents in Forage Rape (*Brassica napus* L.)", *Theor. Appl. Genet.*, 72:706–709, (1986).

Pellan–Delourme, R., Eber, F., Renard, M., 1987, "Male Fertility Restorer in *Brassica napus* With Radish Cytoplasmic Male Sterility", Proc. 7th Int. Rapeseed Conf., Paznan, Poland: 199–203.

Pellan–Delourme, R. and Renard, M. 1998, "Cytoplasmic Male Sterioity in Rapeseed (*Brassica napus* L.): Female Fertility of Restored Rapeseed With "Ogura" and Cybrids Cytoplasma", *Genome* 30:234–238.

Pelletier G., C. Primard, "Molecular, Phenotypic and Genetic Characterization of Mitochondrial Recombinatnts in Rapeseed", Proc. 7th Int. Rapeseed Conf., Poznau, Poland, 113–118 (1987).

Rakow, G. and D. I. McGregor, "Opportunities and Problems in Modification of Levels of Rapeseed C18 Unsaturated Fatty Acids", *J. Am. Oil Chem. Soc.*, 50(10): 400–403, (1973).

Ratledge, Colin, Dawson, Peter and Rattray, James, 1984, *Biotechnology for the Oils and Fats Industry*, American Oil Chemists' Society, Champaign. pp. 328.

Robbelen, Gerhard,, "Changes and Limitations of Breeding for Improved Polyenic Fatty Acids Content in Rapeseed", (Chapter 10) in *Biotechnology for the Oils and Fats Industry*, edited by Colin Ratledge, Peter Dawson and James Rattray, American Oil Chemist' Society, (1984).

Robbelen, G. and A. Nitsch., "Genetical and Physiological Investigations on Mutants for Polyenic Fatty Acids in Rapeseed, *Brassica napus* L.", Z. Planzenzuchtg., 75:93–105, (1975).

Sosulski, F., and K. Dabrowski., "Determination of Glucosinolates in Canola Meal and Protein Products by Desulfation and Capillary Gas–Liquid Chromatography", *J. Agric. Food Chem.*, 32:1172–1175 (1984).

Stefnsson, B. R., "The Development of Improved Rapeseed Cultivars", (Chapter 6) in *High and Low Eurcic Acid Rapeseeds Oils*, edited by John K. G. Kramer, 1983.

\* cited by examiner

Figure 1: Origin of the Low Glucosinolate Restorer Line, 96FNW-1822

| Gen | Materials/Activities | Total Glucs* | Rf Gene Status |
|---|---|---|---|
| F1 | R40 x PRESTOL<br>↓ [self-pollination = sp] | - | all Rr** |
| F2 | 94CWN-2134<br>↓ [sp single plants, harvest, gluc selection] | - | 1 RR : 2 Rr : 1 rr |
| F3 | 95FNW-7763<br>↓ [sp single plants, harvest gluc selection] | <25*** | Rr |
| F4 | 96FNW-1822<br>↓ [sp single plants, harvest, gluc analysis, by HPLC] | <18*** | RR |
| F5 | 96FNW-1822-01**** | 12.31 | Rr |
|  | 96FNW-1822-02 | 11.82 | RR |
|  | 96FNW-1822-03 | 8.48 | Rr |
|  | 96FNW-1822-04 | 8.80 | Rr |
|  | 96FNW-1822-05 | 10.94 | RR |
|  | 96FNW-1822-06 | 11.49 | Rr |
|  | 96FNW-1822-07 | 8.82 | RR |
|  | 96FNW-1822-08 | 8.54 | RR |
|  | 96FNW-1822-09 | 7.90 | Rr |
|  | 96FNW-1822-10 | 9.87 | Rr |

* Total glucosinolates = alkenyl + MSGL + indole
** RR = homozygous Rf fertile; Rr = heterozygous Rf fertile; rr = sterile
*** selection by qualitative method (Palladium) compared to checks at level shown
**** Single plant selection from 96FNW-1822; glucosinolate analysis by HPLC on field harvested seed

Figure 2: Origin of the Low Glucosinolate Restorer Line, 96FNW-1348

| Gen | Materials/Activities | Total Glucs* | Rf Gene Status |
|---|---|---|---|
| F1 | R40 x EUROL | - | all Rr** |
|  | [self-pollination = sp] |  |  |
| F2 | 94CWN-2132 | - | 1 RR : 2 Rr : 1 rr |
|  | [sp single plants, harvest, gluc selection] |  |  |
| F3 | 95FNW-7456 | <25*** | Rr |
|  | [sp single plants, harvest gluc selection] |  |  |
| F4 | 96FNW-1348 | <18*** | Rr |
|  | [sp single plants, harvest, gluc analysis, by HPLC] |  |  |
| F5 | 96FNW-1348-01 **** | 16.59 | RR |
|  | 96FNW-1348-04 | 17.33 | RR |
|  | 96FNW-1348-06 | 13.48 | RR |
|  | 96FNW-1348-07 | 18.89 | RR |

\* Total glucosinolates = alkenyl + MSGL + indole
\*\* RR = homozygous Rf fertile; Rr = heterozygous Rf fertile; rr = sterile
\*\*\* selection by qualitative method (Palladium) compared to checks at level shown
\*\*\*\* Single plant selection from 96FNW-1348; glucosinolate analysis by HPLC on field harvested seed

Figure 3: Origin of the Low Glucosinolate Restorer Line, 96FNW-1628

| Gen | Materials/Activities | Total Glucs* | Rf Gene Status |
|---|---|---|---|
| F1 | R40 x EUROL | - | all Rr** |
|   | [self-pollination = sp] | | |
| F2 | 94CWN-2132 | - | 1 RR : 2 Rr : 1 rr |
|   | [sp single plants, harvest, gluc selection] | | |
| F3 | 95FNW-7387 | <25*** | Rr |
|   | [sp single plants, harvest gluc selection] | | |
| F4 | 96FNW-1628 | <18*** | Rr |
|   | [sp single plants, harvest, gluc analysis, by HPLC] | | |
| F5 | 96FNW-1628-02**** | 10.13 | RR |
|   | 96FNW-1628-03 | 18.36 | RR |
|   | 96FNW-1628-05 | 16.48 | RR |

\* Total glucosinolates = alkenyl + MSGL + indole
\*\* RR = homozygous Rf fertile; Rr = heterozygous Rf fertile; rr = sterile
\*\*\* selection by qualitative method (Palladium) compared to checks at level shown
\*\*\*\* Single plant selection from 96FNW-1628; glucosinolate analysis by HPLC on field harvested seed

Figure 4: Origin of the Low Glucosinolate Restorer Line, 96FNW-1792

| Gen | Materials/Activities | Total Glucs* | Rf Gene Status |
|---|---|---|---|
| F1 | R40 x BRISTOL | - | all Rr** |
|  | [self-pollination = sp] |  |  |
| F2 | 94CWN-2133 | - | 1 RR : 2 Rr : 1 rr |
|  | [sp single plants, harvest, gluc selection] |  |  |
| F3 | 95FNW-7703 | <25*** | Rr |
|  | [sp single plants, harvest gluc selection] |  |  |
| F4 | 96FNW-1792 | <18*** | Rr |
|  | [sp single plants, harvest, gluc analysis, by HPLC] |  |  |
| F5 | 96FNW-1792-02 **** | 16.47 | RR |
|  | 96FNW-1792-03 | 14.40 | RR |
|  | 96FNW-1792-04 | 18.13 | RR |

\* Total glucosinolates = alkenyl + MSGL + indole
\** RR = homozygous Rf fertile; Rr = heterozygous Rf fertile; rr = sterile
\*** selection by qualitative method (Palladium) compared to checks at level shown
\**** Single plant selection from 96FNW-1792; glucosinolate analysis by HPLC on field harvested seed

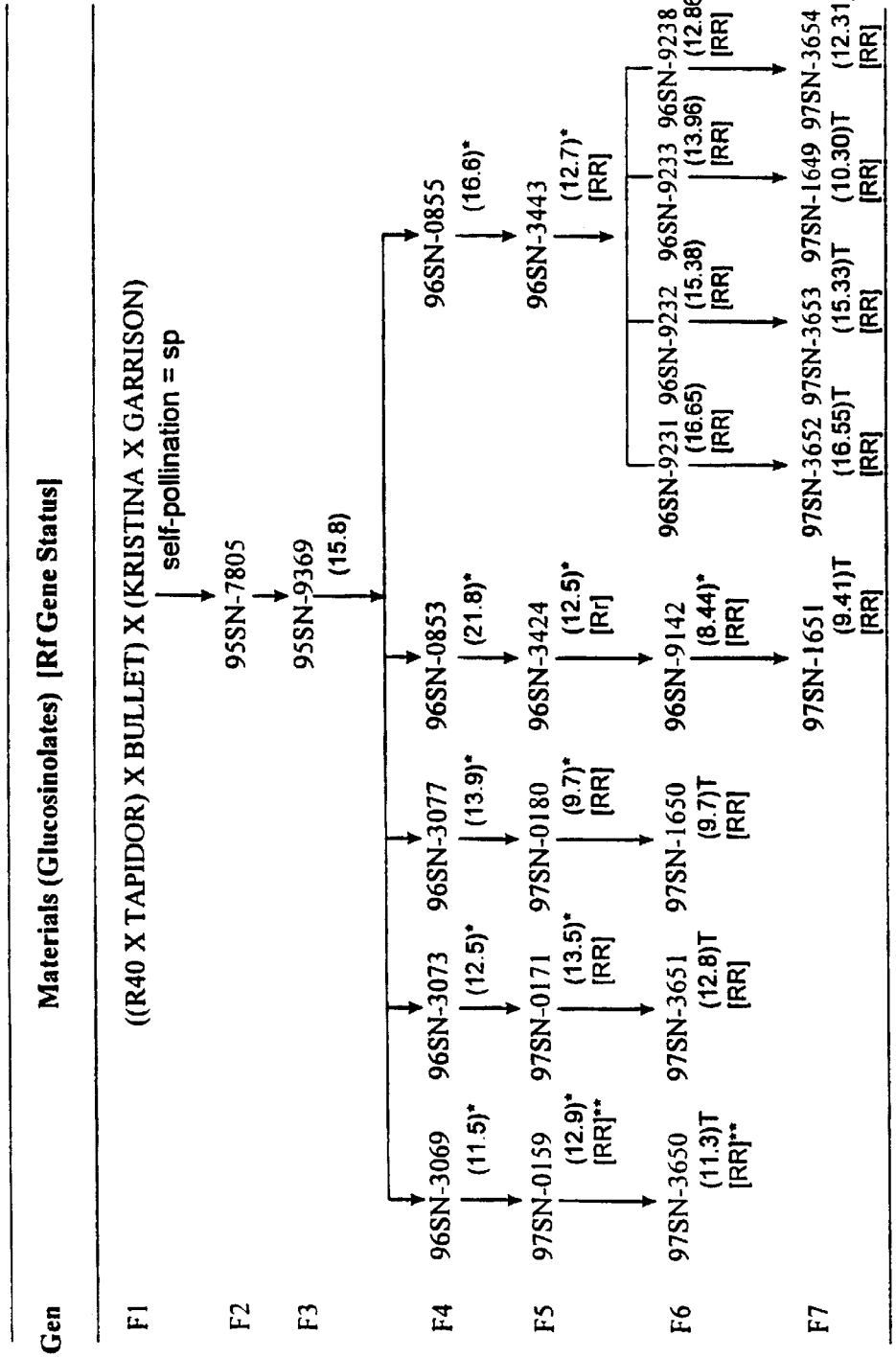

OILSEED BRASSICA CONTAINING AN IMPROVED FERTILITY RESTORER GENE FOR OGURA CYTOPLASMIC MALE STERILITY

This application is a 371 of PCT/CA97/01005, filed Dec. 19, 1997, which has a priority date of Dec. 24, 1996.

BACKGROUND OF THE INVENTION

Oilseed from Brassica plants is an increasingly important crop. As a source of vegetable oil, it presently ranks behind only soybeans and palm in commercial importance and it is comparable with sunflowers. The oil is used both as a salad oil and as a cooking oil.

In its original form, Brassica oil, known as rapeseed oil, was harmful to humans due to its relatively high level of erucic acid, Erucic acid is commonly present in native cultivars in concentrations of 30 to 50 percent by weight based upon the total fatty acid content. This problem was overcome when plant scientists identified a germplasm source of low erucic acid rapeseed oil (Stefansson, 1983).

In addition, plant scientists have attempted to improve the fatty acid profile for rapeseed oil (Robbelen, 1984; Ratledge et al., 1984; Robbelen et al., 1975; and Rakow et al., 1973). These references are representative of those attempts.

Particularly attractive to plant scientists were so-called "double-low" varieties: those low in erucic acid in the oil and low in glucosinolates in the solid meal remaining after oil extraction (i.e., an erucic acid content of less than 2 percent by weight based upon the total fatty acid content, and a glucosinolate content of less than 30 $\mu$mol/gram of the oil-free meal). These higher quality forms of rape, first developed in Canada, are known as canola.

More recently, plant scientists have focused their efforts on reducing the glucosinolate content further, to levels of less than 20 $\mu$mol/gram of oil-free meal, as verified by quantifying trimethylsilyl (TMS) derivatives (Sosulski and Dabrowski, 1984) for spring canola, or less than 20 $\mu$mol/gram of whole, ground seed, as determined by high performance liquid chromatography (HPLC) (International Organization for Standardization, reference number ISO 9167-30 1:1992(E)) for winter canola.

Glucosinolates are sulfur-based compounds that remain in the solid component of the seed—the solid meal—after the seed has been ground and its oil has been extracted. Their structure includes glucose in combination with aliphatic hydrocarbons (3-butenyl glucosinolate, 4-pentenyl glucosinolate, 2-hydroxy-3-butenyl glucosinolate, and 2-hydroxy-4-pentenyl glucosinolate) or aromatic hydrocarbons (3-indoylmethyl glucosinolate, 1-methoxy-3-indoyl methyl glucosinolate). Aliphaitic glucosinolates are also known as alkenyl glucosinolates. Aromatic glucosinolates are also known as indoles.

High levels of glucosinolates are undesirable because they produce toxic by-products when acted upon by the enzyme myrosinase. Myrosinase is a naturally occurring enzyme present in Brassica species. When Brassica seed is crushed, myrosinase is released and catalyzes the breakdown of glucosinolates to produce glucose, thiocyanates, isothiocyanate and nitriles. When separated from glucose, these other products are toxic to certain mammals. Isothiocyanate, for example, inhibits synthesis of thryroxine by the thyroid and has other anti-metabolic effects (Paul et al., 1986). Attempts have been made to inactivate the enzyme myrosinase (using steam, for example). These attempts have not been entirely successful.

Rapeseed possesses high levels of glucosinolates (from 100 $\mu$mol/gram to 200 $\mu$mol/gram of oil-free meal), whereas canola possesses lower levels of glucosinolates (less than 30 $\mu$mol/gram of oil-free meal). The levels of glucosinolates in canola are regulated in many countries. In Europe, for example, winter canola must have a glucosinolate content of less than 25 $\mu$mol/gram of seed at 8.5% moisture, as measured by HPLC. In Canada, spring canola must have a glucosinolate content of less than 30 $\mu$mol/gram of oil-free meal at 0% moisture, as measured by TMS. Many countries are requiring even lower levels of glucosinolates in order to register canola varieties.

In developing improved new Brassica varieties, breeders use self-incompatible (SI), cytoplasmic male sterile (CMS) and nuclear male sterile (NMS) Brassica plants as the female parent. In using these plants, breeders are attempting to improve the efficiency of seed production and the quality of the $F_1$ hybrids and to reduce the breeding costs. When hybridisation is conducted without using SI, CMS or NMS plants, it is more difficult to obtain and isolate the desired traits in the progeny ($F_1$ generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS Brassica female parent, with a pollen producing male Brassica parent. To reproduce effectively, however, the male parent of the $F_1$ hybrid must have a fertility restorer gene (Rf gene). The presence of a Rf gene means that the $F_1$ generation will not be completely or partially sterile, so that either self-pollination or cross pollination may occur. Self pollination of the $F_1$ generation to produce several subsequent generations is important to ensure that a desired trait is heritable and stable and that a new variety has been isolated.

One Brassica plant which is cytoplasmic male sterile and is used in breeding is ogura (OGU) cytoplasmic male sterile (R. Pellan-Delourme et al., 1987). A fertility restorer for ogura cytoplasmic male sterile plants has been transferred from *Raphanus sativus* (radish) to Brassica by Institut National de Recherche Agricole (INRA) in Rennes, France (Pelletier et al., 1987). The restorer gene, Rf1 originating from radish, is described in WO 92/05251 and in Delourme et al., (1991).

However, this restorer is inadequate in that restorer inbreds and hybrids carrying this Rf gene have elevated glucosinolate levels and the restorer is closely related to a decrease in seed set—the number of ovules per silique—(Pellan-Delourme et al., 1988; Delourme et al., 1994). In the case of hybrids, the glucosinolate levels are elevated even when the female parent has reduced glucosinolate content. These levels, typically more than 30 $\mu$mol/gram of oil-free meal, exceed the levels of glucosinolates allowable for seed registration by most regulatory authorities in the world. Thus, the restorer can be used for research purposes, but not to develop directly canola-quality commercial hybrid varieties. To date, there is no other source of a restorer of fertility for ogura cytoplasmic male sterility available.

INRA outlines the difficulties associated with obtaining restorer lines with low glucosinolate levels for ogura cytoplasmic sterility (Delourme, et al., 1994; Delourme, et al., 1995). INRA indicates that these difficulties are due to the linkage between male fertility restoration and glucosinolate content in its breeding material. INRA suggests that more radish genetic information needs to be eliminated in its restorer lines (Delourme, et al., (1995)). Although improvements have been made to restorers during the past few years, isozyme studies performed on the improved restorer lines indicate that radish genetic information still remains around the restorer gene (Delourme et al., 1994).

INRA has attempted to develop a restorer having decreased glucosinolate levels. It reported a heterozygous restorer with about 15 μmol per gram (Delourme et al., 1995). However, (i) this restorer was heterozygous (Rfrf) not homozygous (RfRf) for the restorer gene, (ii) this restorer was a single hybrid plant rather than an inbred line, (iii) there was only a single data point suggesting that this restorer had a low glucosinolate level rather than multiple data points to support a low glucosinolate level, (iv) there was no data to demonstrate whether the low glucosinolate trait was passed on to the progeny of the restorer, and (v) the restorer was selected and evaluated in a single environment—the low glucosinolate trait was not demonstrated to be stable in successive generations in field trials. INRA has not introduced commercially any homozygous restorer having low glucosinolate levels. Its restorer (reported in Delourme et al., 1995) cannot be used to develop restorer inbreds or single cross hybrids products (where the restorer is used as a male inbred) with decreased glucosinolate levels for commercial development.

Canadian patent application 2,143,781 of Yamashita, et al., published on Sep. 11, 1995, claims a hybrid breeding method for crop plants in the family Brassicaceac in which an $F_1$ seed is produced by crossing the female parent of a self-incompatible male sterile line with a male parent. In one embodiment, the male parent possesses a fertility restorer gene. The fertility restorer gene (IM-B) is for MS-N1-derived cytoplasm and was derived from a winter variety (IM line). This was then crossed with a spring double-low line (62We). Although this restorer is alleged to result in low glucosinolate levels, it is not a restorer for ogura cytoplasmic male sterility.

Other breeders have attempted to introduce Rf genes from radish into rapeseed plants by means of intergeneric crossing. However, these crosses have not been employed practically. Canadian patent application 2,108,230 of Sakai, et al, published on Oct. 12, 1993, claims a fertility restorer gene of a Raphanus plant which is introduced into a Brassica plant by cell fusion or intergeneric cross. This application does not disclose (1) a restorer of ogura cytoplasmic male sterility which maintains decreased glucosinolate levels in the oilseed of an $F_1$ generation or (2) the advantageous use of a restorer to develop restorer inbreds and to develop single cross hybrid combinations for commercial products (where the restorer is used as a male inbred).

To attempt to avoid the high glucosinolate content of INRA's restorer of ogura cytoplasmic male sterility, INRA and Serasem (UNCAC) have developed a *Brassica napus* variety called SYNERGY®. SYNERGY is a cross of ogura cytoplasmic male sterile SAMOURAI® (bred by INRA) and male fertile FALCON® (bred by NPZ). FALCON does not carry the restorer gene for ogura cytoplasmic male sterility. Therefore, the $F_1$ hybrid is male sterile. SYNERGY is sold as a "composite hybrid line" (CHL) which consists of a blend of roughly 80% male sterile $F_1$ hybrid (SYNERGY) and 20% male fertile (FALCON), which provides pollen for seed-set on the male sterile $F_1$ plants in the farmer's field.

There are a number of difficulties, however, in relying upon a composite hybrid line. The most important are: (1) that *Brassica napus* is a self-pollinating species, so under poor pollination conditions (such as prolonged cool, wet weather) there may be inadequate pollen movement from the male fertile plants to the $F_1$ hybrid plants, resulting in poor seed set and yield, and (2) that the $F_1$ hybrid plants are more vigorous than the FALCON plants, so the former may outcompete the latter, resulting in too little pollen being available for optimal seed set and yield on the $F_1$ plants.

To date, no one has been able to develop an improved restorer having a homozygous (fixed) restorer gene (RfRf) for ogura cytoplasmic male sterility whose oilseeds have low glucosinolate levels. The restorer must be homozygous (RfRf) so that it can be used to develop restorer inbreds or, as male inbreds, in making single cross hybrid combinations for commercial product development. Ideally, glucosinolate levels would be well below those set out in standards for canola in various countries. That way, breeders could use the improved restorer to produce Brassica inbreds and hybrids having oilseeds with low glucosinolate levels. This would benefit farmers, who could then plant Brassica hybrids which, following pollination, would yield oilseeds having low glucosinolate levels and other desirable characteristics.

In many counties, oilseeds produced by farmers for crushing or for export are not checked for their glucosinolate content. Sometimes a particular lot of canola may have high glucosinolate content, resulting in contamination of the bulk grain to which the poor quality canola is added. It would be an improvement if the glucosinolate content of oilseeds was well below the standards set by various countries in order to avoid contamination of the bulk grain.

Thus, there remains a need for an improved Brassica plant which is a homozygous restorer of fertility for ogura cytoplasmic male sterility and which produces an oilseed with low glucosinolate content. To date, Brassica plants which are restorers of fertility for ogura cytoplasmic male sterility (i) have been heterozygous, rather than homozygous (fixed), for the restorer trait, or (ii) have not produced oilseeds with low glucosinolate content. Indeed, glucosinolate content of such oilseeds has been higher than 30 μmol/gram of oil-free meal.

It is an object of the present invention to provide an improved mature Brassica plant which is a homozygous restorer for ogura cytoplasmic male sterility and which has a glucosinolate content of less than 30 μmol/gram of seed. This restorer could be used to produce restorer inbreds or hybrids with low glucosinolate content. This would allow production of fully-restored, single cross hybrids with genetically-low glucosinolate content in both the hybrid seed and in the oilseed harvested from the hybrid plants.

It is an object of the present invention to provide a Brassica oilseed of the Brassica plant containing a nuclear restorer for ogura cytoplasmic male sterility and having an improved glucosinolate level.

It is another object of the present invention to provide improved Brassica inbred lines, using the restorer. Another object is to use the restorer as a male inbred in making single cross hybrid combinations to develop commercial products.

It is another object of the present invention to provide an oil and edible vegetable meal having an improved glucosinolate level following simple crushing and extraction.

These and other objects and advantages of the invention will be apparent to those skilled in the art from a reading of the following description and appended claims.

SUMMARY OF THE INVENTION

This invention relates to a Brassica plant comprising a homozygous fertility restorer gene for ogura cytoplasmic male sterility, wherein upon pollination the plant yields oilseeds having a total glucosinolate content of not more than 30 µmol per gram, 25 µmol per gram or 20 µmol per gram.

The oilseed of a Brassica plant comprising a homozygous fertility restorer gene for ogura cytoplasmic male sterility and having a glucosinolate content of less than than 30 µmol per gram, 25 µmol per gram or 20 µmol per gram, may be used for preparing oil and/or meal.

This invention also relates to a Brassica plant comprising a homozygous fertility restorer gene for ogura cytoplasmic male sterility, wherein upon pollination the plant yields oilseeds having (i) a total glucosinolate content of not more than 30 µmol per gram and an erucic acid content of no more than 2 percent by weight based upon the total fatty acid content, (ii) a total glucosinolate content of not more than 25 µmol per gram and an erucic acid content of no more than 2 percent by weight based upon the total fatty acid content or (iii) a total glucosinolate content of not more than 20 µmol per gram and an erucic acid content of no more than 2 percent by weight based upon the total fatty acid content.

The Brassica plant may be *Brassica napus, Brassica campestris* or *Brassica juncea*. It may be designated as 95SN-9369, 96FNW-1792, 96FNW-1822, 96FNW-1348, 96FNW-1628 or their sub-lines. The sub-lines may be selected from a group consisting of 97SN-1650 (sub-line of 95SN-9369), 97SN-1651 (sub-line of 95SN-9369), 96FNW1792-03 (sub-line of 96FNW-1792), 96FNW1822-07 (sub-line of 96FNW1822) and 96FNW1822-08 (sub-line of 96FNW1822).

An inbred Brassica plant may be produced using this plant. A hybrid Brassica plant may be produced using this plant. Upon pollination, the inbred or hybrid plant yields oilseed having a total glucosinolate content of (i) not more than 30 µmol per gram, (ii) not more than 25 µmol per gram, or (iii) not more than 20 µmol per gram.

This invention also includes an oilseed of the Brassica plant or from the inbred or hybrid Brassica plant. The oilseed may be present as a component of a substantially homogeneous assemblage of oilseeds which possess the specified glucosinolate content. Oil of the oilseed is also part of this invention. The oilseed may be formed on *Brassica napus, Brassica campestris* or *Brassica juncea*. The mature Brassica oilseed is capable of yielding an endogenous vegetable oil having a glucosinolate content of no more than (i) 30 µmol per gram, (ii) 25 µmol per gram, or (iii) 20 µmol per gram.

Meal which is substantially oil free and which is produced from this oilseed is also part of this invention. The meal has a glucosinolate content of no more than (i) 30 µmol per gram, (ii) 25 µmol per gram, or (iii) 20 µmol per gram.

This invention also relates to a part of the Brassica plant of this invention. The plant part may be selected from a group consisting of nucleic acid sequences (RNA, mRNA, DNA, cDNA), tissue, cells, pollen, ovules, roots, leaves, oilseeds, microspores, vegetative parts, whether mature or embryonic.

The Brassica plant of this invention may be used to breed a novel Brassica line. The breeding may be selected from a group consisting of isolation and transformation, conventional breeding, pedigree breeding, crossing, self-pollination, haploidy, single seed descent and backcrossing.

BRIEF DESCRIPTION OF THE DRAWINGS

The invention will now be described in relation to the figures in which:

FIG. 1 illustrates by way of exemplification the formation of new *Brassica napus* plant material in accordance with the present invention designated 96FNW-1822 as described in greater detail in Example 3.

FIG. 2 illustrates by way of exemplification the formation of new *Brassica napus* plant material in accordance with the present invention designated 96FNW-1348 as described in greater detail in Examples 3 and 4.

FIG. 3 illustrates by way of exemplification the formation of new *Brassica napus* plant material in accordance with the present invention designated 96FNW-1628 as described in greater detail in Example 3.

FIG. 4 illustrates by way of exemplification the formation of new *Brassica napus* plant material in accordance with the present invention designated 96FNW-1792 as described in greater detail in Example 1 and 2.

FIG. 5 illustrates by way of exemplification the formation of new *Brassica napus* plant material in accordance with the present invention designated 95SN-9369 and its Descendants (97SN-1650, 97SN-1651 and others) as described in greater detail in Example 6.

DESCRIPTION OF PREFERRED EMBODIMENTS

Methods for Determining Glucosinolates—The glucosinolate levels discussed herein are determined in accordance with two standard procedures, namely (1) high performance liquid chromatography (HPLC), as described in ISO 9167-1:1992(E), for quantification of total, intact glucosinolates, and (2) gas-liquid chromatography for quantification of trimethylsilyl (TMS) derivatives of extracted and purified desulfoglucosinolates, as described by Sosulski and Dabrowski (1984). Both the HPLC and TMS methods for determining the glucosinolate levels discussed herein involve analysis of the solid component of the seed after crushing and oil extraction, (i.e., the de-fatted or oil-free meal).

Method for Determining Fatty Acid Profile—The fatty acid concentrations discussed herein are determined in accordance with a standard procedure wherein the oil is removed from the Brassica oilseeds by crushing and is extracted as fatty acid methyl esters following reaction with methanol and sodium methoxide. Next the resulting ester is analyzed for fatty acid content by gas liquid chromatography using a capillary column which allows separation on the basis of the degree of unsaturation and chain length. This analysis procedure is described in the work of J. K. Daun et al, 1983, which is herein incorporated by reference.

Statement of Invention—A novel edible endogenous vegetable meal is obtained from an improved Brassica oilseed that possesses glucosinolate and, optionally, erucic acid, in a low concentration. The Brassica oilseed contains the homozygous nuclear restorer gene for ogura cytoplasmic male sterility. Fewer glucosinolates are subjected to the enzyme myrosinase, which produces toxic by-products. The novel edible endogenous meal of the present invention is formed by the simple crushing of the Brassica oilseeds and the simple physical separation of the solid component of the seed—the solid meal—from the oil component.

The Brassica oilseeds of the present invention possess a glucosinolate content in the solid component before crushing and extraction of the oil component of less than 30 µmol/gram, and most preferably, less than 20 µmol/gram. The glucosinolate content may be any one or a mixture of alkenyl (3-butenyl glucosinolate, 4-pentenyl glucosinolate, 2-hydroxy-3-butenyl glucosinolate, and 2-hydroxy-4- pentenyl glucosinolate), MSGL (methylthiobutenyl glucosinolate and methylthiopentenyl glucosinolate) and indole (3-indoylmethyl glucosinolate and 1-methoxy-3-indoylmethyl glucosinolate). The glucosinolate determination preferably is made on the air-dry-oil-free solid as measured by the gas liquid chromatography (TMS-based) method of the Canadian Grain Commission. The glucosinolate levels commonly are made possible by selecting starting materials which already are known to form the desired glucosinolate content, and by making selections which retain this value following combination with the recited traits.

Generating Inbred Plants Using Restorer—The restorer Brassica plant of this invention may be used for inbreeding using known techniques. The homozygous restorer gene of the Brassica plant can be introduced into Brassica inbred lines by repeated backcrosses of the Brassica plant. For instance, the resulting oilseeds may be planted in accordance with conventional Brassica-growing procedures and following self-pollination Brassica oilseeds are formed thereon. Again, the resulting oilseeds may be planted and following self-pollination, next generation Brassica oilseeds are formed thereon. The initial development of the line (the first couple of generations of the Brassica oilseed) preferably is carried out in a greenhouse in which the pollination is carefully controlled and monitored. This way, the glucosinolate content of the Brassica oilseed for subsequent use in field trials can be verified. In subsequent generations, planting of the Brassica oilseed preferably is carried out in field trials. Additional Brassica oilseeds which are formed as a result of such self-pollination in the present or a subsequent generation are harvested and are subjected to analysis for the desired trait, using techniques known to those skilled in the art.

Generating Hybrid Plants Using Restorer as Male Parent—This invention enables a plant breeder to incorporate the desirable qualities of an ogura restorer of cytoplasmic male sterility into a commercially desirable Brassica hybrid variety. Brassica plants may be regenerated from the ogura restorer of this invention using known techniques. For instance, the resulting oilseeds may be planted in accordance with conventional Brassica-growing procedures and following cross-pollination Brassica oilseeds are formed on the female parent. The planting of the Brassica oilseed may be carried out in a greenhouse or in field trials. Additional Brassica oilseeds which are formed as a result of such cross-pollination in the present generation are harvested and are subjected to analysis for the desired trait. *Brassica napus, Brassica campestris,* and *Brassica juncea* are Brassica species which could be used in this invention using known techniques.

The hybrid may be a single-cross hybrid, a double-cross hybrid, a three-way cross hybrid, a composite hybrid, a blended hybrid, a fully restored hybrid and any other hybrid or synthetic variety that is know to those skilled in the art, using the restorer of this invention.

In generating hybrid plants, it is critical that the female parent ($P_1$) that is cross-bred with the ogura restorer ($P_2$) have a glucosinolate level that is sufficiently low to ensure that the seed of the $F_1$ hybrid has glucosinolate levels within regulatory levels. The glucosinolate level of the seed harvested from the $F_1$ hybrid is roughly the average of the glucosinolate levels of the female parent $P_1$) and of the male parent ($P_2$). The glucosinolate level of the hybrid grain ($F_2$) is reflective of the genotype of the $F_1$ hybrid. For example, if the objective is to obtain hybrid grain ($F_2$) having a glucosinolate level of less than 20 $\mu$mol/gram, and the male parent (ogura restorer) has a glucosinolate level of 15 $\mu$mol/gram, the female parent must have a glucosinolate level of less than 25 $\mu$mol/gram.

Generating Plants from Plant Parts—Brassica plants may be regenerated from the plant parts of the restorer Brassica plant of this invention using known techniques. For instance, the resulting oilseeds may be planted in accordance with conventional Brassica-growing procedures and following self-pollination Brassica oilseeds are formed thereon. Alternatively, doubled haploid plantlets may be extracted to immediately form homozygous plants.

Vegetable meal—In accordance with the present invention it is essential that the edible endogenous vegetable meal of the Brassica oilseed contain glucosinolate levels of not more than 30 $\mu$mol/gram of seed. The female parent which can be used in breeding Brassica plants to yield oilseed Brassica germplasm containing the requisite genetic determinant for this glucosinolate trait is known and is publicly available. For instance, Brassica germplasm for this trait has been available in North America since the mid-1970's.

Representative winter rape varieties that include the genetic means for the expression of low glucosinolate content and that are commercially available in Europe, for example, include, PRESTOL®, EUROL®, BRISTOL® (each available from Semences Cargill), TAPIDOR®, SAMOURAI® (available from Serasem). Representative spring rape varieties that include the genetic means for the expression of low glucosinolate content and that are commercially available in Canada, for example, include BULLET®, GARRISON® and KRISTANA® (each available from Svalof Weibull).

Other winter rape varieties that include the genetic means for the expression of low glucosinolate content and that are commercially available in Europe include APEX® GOELAND®, FALCON®, LIRAJET®, CAPITOL® and EXPRESS®.

Also, genetic means for the expression of low glucosinolate trait can be obtained from American Type Culture Collection, Rockville, Md. 20852. Seeds were deposited with the ATCC, comprising restorer line 97SN-1650 (Accession No. ATCC 97838), 97SN-1651 (Accession No. ATCC 97839), 96FNW1792-03 (Accession No. ATCC 209001) and 96FNW1822-07 (Accession No.209002), discussed hereafter. Such low levels of glucosinolates in the oilseed Brassica serve to impart increased commercial value to the meal.

The edible endogenous vegetable oil of the Brassica oilseeds contains fatty acids and other traits that are controlled by genetic means (see U.S. patent application entitled, "Improved Oilseed Brassica Bearing An Endogenous Oil Wherein the Levels of Oleic, Alpha-Linolenic and Saturated Fatty Acids Are Simultaneously Provided In An Atypical Highly Beneficial Distribution Via Genetic Control", of Pioneer Hi-Bred International, Inc., WO91/15578; and U.S. Pat. No. 5,387,758, incorporated herein by reference.) Preferably erucic acid of the Brassica oilseed is included in a low concentration of no more than 2 percent by weight based upon the total fatty acid content that is controlled by genetic means in combination with the other recited components as specified. The genetic means for the expression of such erucic acid trait can be derived from numerous commercially available canola varieties having good agronomic characteristics, such as 46A05, 46A65, BOUNTY®, CYCLONE®, DELTA®, EBONYY®, GARRISON®, IMPACT®, LEGACY®, LEGEND®, PROFIT® and QUANTUM®. Each of these varieties is registered in Canada and is commercially available in that country.

Herbicide Resistance—As is known to those skilled in the art, it is possible to use this invention to develop a Brassica plant which is a restorer of fertility for ogura cytoplasmic male sterility, produces oilseeds having low glucosinolate content and has other desirable traits. Additional traits which are commercially desirable are those which would reduce the cost of production of the Brassica crop or which would increase the quality of the Brassica crop. Herbicide resistance, for example, is a desirable trait (see Example 4-1 and 4-2 in which ogura restorer lines with low glucosinolate content and different types of herbicide resistance have been developed).

If desired, a genetic means for tolerance to a herbicide when applied at a rate which is capable of destroying rape plants which lack said genetic means optionally may also be incorporated in the rape plants of the present invention as described in commonly assigned U.S. Pat. No. 5,387,758, that is herein incorporated by reference.

Breeding Techniques—It has been found that the combination of desired traits described herein, once established, can be transferred into other plants within the same *Brassica napus, Brassica campestris,* or *Brassica juncea* species by conventional plant breeding techniques involving cross-pollination and selection of the progeny. It surprisingly has been demonstrated that the restorer gene in combination with low glucosinolate levels is highly heritable, can be transmitted to progeny, and can be recovered in segregating progeny in subsequent generations following crossing.

Also, once established the desired traits can be transferred between the *napus, campestris,* and *juncea* species using the same conventional plant breeding techniques involving pollen transfer and selection. The transfer of traits between Brassica species, such as *napus* and *campestris,* by standard plant breeding techniques is already well documented in the technical literature. (See, for instance, Tsunada et al., 1980).

As an example of the transfer of the desired traits described herein from *napus* to *campestris,* one may select a commercially available *campestris* variety such as REWARD®, GOLDRUSH®, and KLONDIKE®, and carry out an interspecific cross with an appropriate plant derived from a *napus* breeding line, such as that discussed hereafter (i.e., 95SN-9369). Alternatively, other *napus* breeding lines may be reliably and independently developed using known techniques. After the interspecific cross, members of the $F_1$ generation are self-pollinated to produce $F_2$ oilseed. Selection for the desired traits is then conducted on single $F_2$ plants which are then backcrossed with the *campestris* parent through the number of generations required to obtain a euploid (n=10) *campestris* line exhibiting the desired combination of traits.

In order to avoid inbreeding depression (e.g., loss of vigor and fertility) that may accompany the inbreeding of *Brassica campestris,* selected, i.e. $BC_1$ plants that exhibit similar desired traits while under genetic control advantageously can be sib-mated. The resulting oilseed from these crosses can be designated $BC_1SIB_1$ oilseed. Accordingly, the fixation of the desired alleles can be achieved in a manner analogous to self-pollination while simultaneously minimizing the fixation of other alleles that potentially exhibit a negative influence on vigor and fertility.

A representative *Brassica juncea* variety of low glucosinolate content and low erucic acid content into which the desired traits can be similarly transferred include the breeding lines, 96SJ-2690, 96SJ-2691, and 96SJ-2692.

Stand of Plants—The oilseed Brassica plants of the present invention preferably are provided as a substantially uniform stand of plants that are capable of forming oilseeds providing a meal which exhibits the recited improved glucosinolate levels. The Brassica oilseeds of the present invention preferably are provided as a substantially homogeneous assemblage of oilseeds which possess the improved glucosinolate levels.

The improved oilseed Brassica plant of the present invention is capable of production in the field under conventional oilseed Brassica growing conditions that are commonly utilized during oilseed production on a commercial scale. Such oilseed Brassica exhibits satisfactory agronomic characteristics and is capable upon self-pollination of forming oilseeds that possess the glucosinolate levels within the meal present therein. For the purposes of the present invention, "satisfactory agronomic characteristics" is defined as the ability to yield an oilseed harvest under standard field growing conditions having glucosinolate levels that are sufficiently low for registration of canola varieties (suitable for commercial use).

The ability to provide in a single edible endogenous vegetable meal the improved glucosinolate levels of the present invention using the ogura restorer of the present invention, is considered to be totally unexpected. An edible endogenous meal as presently claimed is novel and its production previously eluded all other researchers. One skilled in oilseed Brassica technology reasonably would have concluded that the ogura restorer is genetically linked to the gene regulating glucosinolate levels, i.e. that both genes are on a fragment of Raphanus DNA that has been integrated into a *B. napus* chromosome. Whereas there is no allelic variation within the Raphanus DNA fragment, there is no opportunity for a crossover event to separate the Rf gene from the gene coding for elevated glucosinolate content, thus precluding the simultaneous expression of the restorer and low glucosinolate levels.

The improved edible endogenous vegetable meal of the present invention, in a preferred embodiment, exhibits a satisfactory flavor that can be described as being generally comparable to that of canola meal. Representative uses of the meal include feed for livestock. Representative uses of the oil include salad, frying, cooking, spraying, and viscous-food product applications. Handling and inventory considerations are greatly simplified since the endogenous vegetable meal and oil of the present invention fulfills the requirements for a wide variety of end uses. Each of these benefits is achieved in a straightforward manner in an endogenous product that inherently possesses superior health and nutritional properties.

The following Examples are presented as specific illustrations of the present invention. It should be understood, however, that the invention is not limited to the specific details set forth in the Examples.

EXAMPLE 1

Development of the improved OGURA restorer line, 96FNW-1792, including methodology for glucosinolate determination and assessment of fixity of the Rf gene (see FIG. 4).

| | |
|---|---|
| Generation: | Parent to F1 |
| Time Period: | November, 1992 to April, 1993 |
| Seed Planted: | R40 (original restorer source from INRA) and BRISTOL (commercial winter canola from Semences Cargill, France) |
| Seed Harvested: | F1 = 93CWN-867 (= R40 × BRISTOL) |

Methods: Parents were grown, and all crossing was carried out in a controlled environment in the greenhouse. R40 (restorer source) was used as the female parent so that all resulting materials would carry the OGURA cytoplasm.

| | |
|---|---|
| Generation: | F1 to F2 |
| Time Period: | May, 1993 to November, 1993 |
| Seed Planted: | F1 = 93CWN-867 (= R40 × BRISTOL) |
| Seed Harvested: | F2 = 94CWN-2133 |

Methods: F1 plants were grown out to flowering in the greenhouse. Sterile plants were discarded; fertile plants were self-pollinated to produce F2 seed. At maturity, F2 seed was harvested from each F1 plant separately.

Each F2 seedlot was screened for glucosinolates using the glucose reaction method. The seedlots with the lowest glucosinolate content were bulked to produce the F2 seed of 94CWN-2133 which could be sampled for F3 production.

| | |
|---|---|
| Generation: | F2 to F3 |
| Time Period: | December, 1993 to June, 1994 |
| Seed Planted: | F2 = 94CWN-2133 |
| Seed Harvested: | F3 = 95FNW-7703 (selected F3 line) |

Methods: Five hundred F2 plants from the seedlot, 94CWN-2133, were grown out in the greenhouse. Sterile plants were discarded at flowering, and fertile plants were self-pollinated. At maturity, F3 seed was harvested from each F2 plant individually.

Each F3 seed line was screened for glucosinolate content, using the Palladium method. Seed of checks, grown in the same greenhouse environment as the F3s, was included in this analysis. The F3 seed line, 95FNW-7703, was identified as having less than 25 umol/g total glucosinolate content, so was advanced into the field nursery program.

| | |
|---|---|
| Generation: | F3 to F4 |
| Time Period: | August, 1994 to July, 1995 |
| Seed Planted: | F3 = 95FNW-7703 |
| Seed Harvested: | F4 = 96FNW1792 (selected F4 line) |

Methods: 95FNW-7703 was planted in the restorer selection nursery in Frouville, France in August, 1994. Following emergence, there were ca. 60 plants in a two row nursery plot. Two elite commercial checks, Bristol and Goeland, were included at frequent intervals in the nursery as checks for comparison.

At early flowering, 10 single plants within 95FNW-7703 were self-pollinated by bagging. The fertility of all plants within the line was assessed by scoring pollen production (male fertility) and seed set within developing pods (female fertility). At the end of flowering, the pollination bags were removed.

At maturity, F4 seed was harvested from each of the 10 selfed plants individually. Seed quality on each of the F4 seedlots was assessed; lines with shrivelled and/or mouldy seed were discarded.

Mature, cleaned seed of the remaining F4 lines was analysed for glucosinolate content by the Palladium method, Seed of the Bristol and Goeland checks was harvested, and glucosinolates determined by HPLC. Seed from these checks was included in the Palladium analysis to allow selection of low glucosinolate Rf lines. The average of Bristol and Goeland plus one standard deviation (ca. 18 umol/g total glucosinolates) was used as a culling level. The F4 seed line, 96FNW-1792, had less than 18 umol glucosinolate content, and had the lowest glucosinolate content of any of the 95FNW-7703-derived lines.

The fertility assessment of 95FNW-7703 identified no sterile plants in a sample of ca. 50 individuals. As the Rf gene is a single, dominant gene, if 95FNW-7703 was segregating for the Rf gene, steriles would be expected in a frequency of 0.25 with perfect sampling. Statistically, the probability of finding no steriles in a sample of 50 if the line is segregating is 0.000000562. Based on this, we can conclude that 95FNW-7703 is fixed for the Rf gene, meaning that it was derived from an F2 plant which was homozygous Rf.

EXAMPLE 2

Development of F5 sub-lines of the improved OGURA restorer, 96FNW-1792 (continued from Example 1, see FIG. 4).

Generation: F4 to F5

| | |
|---|---|
| Time Period: | August, 1995 to July, 1996 |
| Seed Planted: | F4 = 96FNW-1792 |
| Seed Harvested: | F5 = 96FNW-1792-02, -03, and -04 |

Methods: 96FNW-1792 was planted in a four row plot in the 1995/96 restorer nursery at Frouville, France. After emergence, there were >100 plants in the nursery plot. BRISTOL and GOELAND were planted as running checks in the nursery.

During the winter of 95/96, the homozygosity of 20 individual plants within 96FNW-1792 was assessed by determining the PGI-2 isozyme phenotype on leaf tissue extract subjected to starch gel electrophoresis, as described by Delourme and Eber (1992). All plants were found to be homozygous for the radish PGI-2 phenotype. Since this phenotype is the product of a PGI-2 allele from radish, which is very tightly linked to the OGURA Rf gene, these results indicate that 96FNW-1792, and the 20 specific plants sampled, are fixed for the Rf gene (RfRf).

At flowering, the 20 selected plants were self-pollinated by bagging. Male and female fertility of all plants within the 96FNW-1792 plot were assessed as described in Example 1. No sterile plants were found in the sample of 100 plants, again indicating that 96FNW-1792 is fixed for the Rf gene. Seed set (number of ovules per silique) was within the normal range for *Brassica napus*. Pollination bags were removed at the end of flowering.

At maturity, seed of each of the 20 plants was harvested individually, threshed and cleaned. The lines with the best seed quality were selected, and total glucosinolate content on these materials was determined by HPLC. The total glucosinolate content (indole+MSGL+alkenyl) for three of the selected sub-lines is given in FIG. 4 (F5 generation).

A sample of 20 plants of each of these three sub-lines was grown out in the greenhouse. Leaf tissue was sampled from each plant within each sub-line, and PGI-2 isozyme analysis carried out. The results indicated that the three lines, and all of the plants within them, are fixed for the Rf gene.

The three sub-lines (96FNW-1792-02, -03, and -04) are currently being finished as restorer inbreds. They are also being used as male inbreds in making numerous single cross hybrid combinations for commercial product development.

EXAMPLE 3

Development of the improved OGURA restorer lines 96FNW-1822, 96FNW-1348, 96FNW-1628 (see FIGS. 1, 2 and 3).

Generations of plants shown in FIGS. 1, 2 and 3 were grown in the time periods and using similar source material and methods indicated in Example 1. Glucosinolate and fertility assessments were conducted as indicated in Example 1. Elite commercial checks were included at frequent intervals as checks for comparison. Again, results of fertility assessments indicated that a number of sub-lines (as shown in FIGS. 1, 2 and 3) were fixed for the Rf gene and had low glucosinolate levels.

Plants of sub-lines of restorer lines 96FNW-1822 and 96FNW-1348 were grown in France during the winter of 1996–97. Sound seed of these plants was assessed for fertility, and analysed for glucosinolate content by HPLC. Fertility observations showed that the sub-lines were fixed for the Rf gene. The HPLC analysis revealed less than 15 uM glucosinolate content in each of these sub-lines. Test crosses were conducted to assess transmission of the restorer gene. Table 1 below illustrates the results of the fertility assessments and glucosinolate content.

TABLE 1

Fertility observations and glucosinolate content of sub-lines grown in 1France during the winter of 1996/97.

| CVN Code (New) | BLN Code (Previous) | Total Glucosinolates (umol/g by HPLC) 1996/97 (France) | No. of fertile and sterile plants in a sample (France, 1997) * | | | |
|---|---|---|---|---|---|---|
| | | | Inbred | | Test Cross | |
| | | | Fertile | Sterile | Fertile | Sterile |
| NW1717 | 96FNW-1822-2 | 8.73 | 2,000 | 0 | 321 | 1 |
| | 96FNW-1822-5 | 10.16 | 2,000 | 0 | 412 | 1 |
| | 96FNW-1822-7 | 8.14 | 2,000 | 0 | 420 | 0 |
| | 96FNW-1822-8 | 9.82 | 2,000 | 0 | 346 | 2 |
| NW1712 | 96FNW-1348-6 | 14.71 | 2,000 | 0 | 375 | 2 |

* Fertile/sterile classification by visual inspection of flower morphology

EXAMPLE 4

Development of the improved OGURA restorer line, 96FNW-1348, which combines low glucosinolate content with desirable agronomic traits and disease tolerance.

The following table shows performance data for four fully-restored, single-cross hybrids involving elite female inbreds and 96FNW-1348. This data was collected from yield trials at nine European locations in the 1995/96 testing season. Comparisons are made to SYNERGY, a composite hybrid-line developed by Serasem, France.

| Hybrid: | Yield (% Chk) | Height | Maturity (1–9)* | Lodging (1–9) | Stem Disease |
|---|---|---|---|---|---|
| 95-90013 | 107% | 163 | 5.0 | 6.5 | 4.2 |
| 95-90002 | 106% | 160 | 4.0 | 7.5 | 5.6 |
| 95-90004 | 106% | 148 | 3.8 | 5.8 | 4.2 |
| 95-90010 | 105% | 165 | 3.9 | 7.5 | 4.6 |
| 95-90006 | 104% | 155 | 4.0 | 7.2 | 4.8 |
| SYNERGY | 100% | 155 | 5.4 | 7.3 | 4.0 |

*maturity, lodging and stem disease scores are on 1–9 scale, where 1 = earliest, most lodging susceptible, most disease susceptible, and 9 = latest, most lodging resistant most disease resistant

EXAMPLE 5

Development of improved OGURA restorer lines with low glucosinolate content, desirable agronomic traits, and herbicide resistance.

5-1: Development of elite OGURA restorer lines with resistance to imidazolinone herbicides:

1. Produce $F_1$ of 96FNW1348 (winter low glucosinolate Rf line)×45A71 (spring Pursuit Smart® variety)
2. Germinate $F_1$ spray seedlings with 100 g/ha of PURSUIT to confirm resistance
3. Produce $BC_1$ $F_1$ by crossing $F_1$ to 96FNW1348
4. Germinate $BC_1$ $F_1$, spray seedlings with 100 g/ha PURSUIT, select 25% of plants with highest level of resistance
5. Produce $BC_1$ $F_2$ by selfing selected plants
6. Germinate $BC_1$ $F_2$, spray seedlings with 400 g/ha PURSUIT, self most resistant plants, harvest $F_3$s
7. Germinate $F_3$ lines, spray with 400 g/ha PURSUIT; select lines in which all plants are resistant, self-pollinate, harvest F4 seed, confirm low glucosinolate content
8. Continue self-pollination with selection in the nursery; testcross selected imidazolinone resistant (IR) restorer inbreds to elite IR female inbreds, then evaluate low glucosinolate IR hybrids in yield trails 5-2: Development of elite OGURA restorer lines with other forms of herbicide resistance, i.e. Roundup Ready®, Liberty Link®:

1. Follow procedures outlined for development of IR inbreds and hybrids, starting with fixed herbicide resistant source
2. Once elite, low glucosinolate, herbicide resistant restorer lines have been identified, these should be used as parents in subsequent cycles, for crossing with other elite source materials. New herbicide resistant, low glucosinolate restorer lines can be isolated from these source materials by haploidy, pedigree breeding, or backcrossing, all of which are methods familiar to those skilled in the art of rapeseed breeding.

EXAMPLE 6

Development of improved OGURA restorer line, designated 95SN-9369 and Descendants (97SN-1650, 97SN-1651 and others) with low glucosinolate content and desirable agronomic traits

| | |
|---|---|
| Generation: | Parent to F1 (two steps: C1 = three-way cross, C2 = complex cross) |
| Time Period: | C1 = January, 1994 to April, 1994; C2 = May, 1994 to August, 1994 |
| Seed Planted: | C1: female = R40 × TAPIDOR ® (winter); male = BULLET ® (spring) C2: female = C1; male = KRISTINA ® × GARRISON ® |

Methods: All materials were grown and crossing was performed in controlled environment greenhouses. The R40× TAPIDOR® F1 used as the female in C1 was from the winter canola breeding program. C2 was made using several fertile C1 plants as female, and a bulk pollen sample from several male plants. The final product of C2 was the complex cross F1, ((R40×TAPIDOR®)×BULLET®)× (KRISTINA®×GARRIFSON®).

| | |
|---|---|
| Generation: | F1 to F2 |
| Time Period: | September to December, 1994 |
| Seed Planted: | F1 = ((R40 × TAPIDOR ®) × BULLET ®) × (KRISTINA ® × GARRISON ® |
| Seed Harvested: | F2 = 95SN-7805 |

Methods: 32 F1 plants were grown to flowering in the greenhouse and self-pollinated to produce F2 seed. At maturity, F2 seed from each F1 plant was harvested separately and analysed for glucosinolate content by thymol method (colorimetric quantification). F2 seedlots with the lowest glucosinolate content, in comparison to a check variety, were selected for further breeding.

| | |
|---|---|
| Generation: | F2 to F3 |
| Time Period: | January, 1995 to April, 1995 |
| Seed Planted: | F2 = 95SN-7805 |
| Seed Harvested: | F3 = 95SN-9369 (selected F3) |

Methods: Several hundred F2 plants were grown out in the greenhouse. At flowering, sterile plants were discarded, and all fertile plants were self-pollinated by bagging. Bags were removed at the end of flowering, and seed was allowed to fully mature on the plants prior to harvest. All F3 seed lines (harvested from individual F2 plants) were screened for glucosinolate content by the thymol method. The F3 seed line, 95SN-9369 was selected as being among the lowest in glucosinolate content.

| | |
|---|---|
| Generation: | F3 to F4 |
| Time Period: | May, 1995 to August, 1995 |
| Seed Planted: | F3 = 95SN-9369 |
| Seed Harvested: | F4 = 96SN-3077, 96SN-0853, and others (see FIG. 5) |

Methods: A large sample of F3 plants from 95SN-9369 was grown to flowering in the greenhouse, and bagged to produce F4 seed. Bags were removed at the end of flowering; F4 seed was harvested from each F3 plant individually at full maturity. Each F4 seed line (seed harvested from a single F3 plant) was analysed for glucosinolate content by the thymol method. Five F4s were selected for further breeding (see FIG. 5), including 96SN-3077 and 96SN-0853.

| | |
|---|---|
| Generation: | F4 to F5 |
| Time Period: | September, 1995 to December, 1995 |
| Seed Planted: | F4 = 96SN-3077, 96SN-0853 and others (see FIG. 5) |
| Seed Harvested: | F5 = 96SN-3424 (from 965N-0853), 97SN-0180 (from 96SN-3077) and others (see FIG. 5 for details). |

Methods: Fifteen plants of each of the selected F4 lines were planted in the greenhouse, along with check varieties (for glucosinolate selection). Each plant was bagged at flowering, bags were removed at the end of flowering and seed was harvested from individual plants at full maturity. Each F5 seed line (seed from a single F4 plant) was analysed for glucosinolate content by the thymol method. The best F5 from each F4 was selected for further breeding.

| | |
|---|---|
| Generation: | F5 to F6 (97SN-0180 was not included in this planting) |
| Time Period: | January, 1996 to April, 1996 |
| Seed Planted: | F5 = 96SN-3424 and others (see FIG. 5) |
| Seed Harvested: | F6 = 96SN-9142 (from 96SN-3424) and others (see FIG. 5 for details) |

Methods: Fifteen plants of each of the selected F5 lines were planted in the greenhouse, along with check varieties (for glucosinolate selection). Each plant was bagged at flowering; bags were removed at the end of flowering and seed was harvested from individual plants at full maturity. Each F6 seed line (seed from a single F5 plant) was analysed for glucosinolate content by the thymol method. The best F6 from each F5 was selected for further breeding.

| | |
|---|---|
| Generation: | Field evaluation - F5 to F6 for 97SN-0180; F6 to F7 for 96SN-9142 |
| Time Period: | May, 1996 to August, 1996 |
| Seed Planted: | F5 = 97SN-0180 |
| | F6 = 96SN-9142 and others (see FIG. 5) |
| Seed Harvested: | F6 = 97SN-1650 |
| | F7 = 97SN-1651 (from 96SN-9142) and others (see FIG. 5 for details) |

Methods: Selected lines were planted in two row plots in an isolation near Hillsburgh, Ontario. After emergence, there were more than 100 plants per line. At flowering, every plant in a selected line was scored for fertility/sterility, and 20 plants were bagged to produce selfed seed. Bags were removed at the end of flowering and seed was harvested at full maturity. Single plants with sound seed were analysed for glucosinolate content by TMS. Fertility observations showed that both 97SN-1651 and 97SN-1650 were fixed (homozygous) for the Rf gene. The TMS analysis revealed less than 15 uM glucosinolate content in both of these lines (see FIG. 5 for precise data). Both lines were observed to have acceptable maturity, standability (lodging resistance) and plant type in the nursery. These lines, and line 97SN-1649, have been advanced into seed production during the winter of 1996/97 in Chile, where they are being crossed to several elite ogura male sterile inbreds (females) to produce single cross hybrids. The resulting hybrids were evaluated in multi-locations trials in western Canada in summer, 1997. Seed from the plants grown in Chile during the winter of 1996/97 were planted in Ontario in 1997. Seeds from the resulting plants were harvested in the summer of 1997 and evaluated for fertility and glucosinolate content. Test crosses were conducted to assess transmission of the restorer gene. The results are shown in Table 2 below.

TABLE 2

Results of fertility observations and glucosinolate analysis of lines 97SN-1649 and 97SN-1650 grown in Chile during 1996–97 and Ontario during the spring of 1997.

| CVN Code (New) | BLN Code (Previous) | Total Glucosinolates ($\mu$mol/g by TMS) 96/97 (Chile) | 1997 (Ontario) | No. of fertile and sterile plants in a sample (Ontario 1997) * | | | |
|---|---|---|---|---|---|---|---|
| | | | | Inbred | | Test Cross | |
| | | | | Fertile | Sterile | Fertile | Sterile |
| NS3059 | 97SN-1649 | 11.45 | 11.32 | 600 | 0 | 38 | 2 |
| NS3060 | 97SN-1650 | 14.40 | 14.01 | 600 | 0 | 42 | 0 |

* Fertile/sterile classification by visual inspection of flower morphology

A person skilled in the art could use the Brassica plant of this invention to develop a Brassica plant which is a restorer of fertility for ogura cytoplasmic male sterility, produces oilseeds having low glucosinolate content and which is resistant to one or more herbicides. Herbicide resistance could include, for example, resistance to the herbicide glyphosate, sold by Monsanto under the trade mark ROUNDUP. Glyphosate is an extremely popular herbicide as it accumulates only in growing parts of plants and has little or no soil residue.

There are two genes involved in glyphosate resistance in canola. One is for an enzyme which detoxifies the herbicide: it is called GOX, glyphosate oxidoreductase. The other is a mutant target gene, for a mutant form of EPSP synthase. One skilled in the art could use GOX or CP4 with promoters in canola. Basically, the genes are introduced into a plant cell, such as a plant cell of this invention carrying the restorer gene for ogura cytoplasmic male sterility, and then the plant cell grown into a Brassica plant.

As another example, a person skilled in the art could use the Brassica plant of this invention to develop a Brassica plant which is a restorer of fertility for ogura cytoplasmic male sterility, produces oilseeds having low glucosinolate content and which is resistant to the family of imidazoline herbicides, sold by Cyanamid under trade-marks such as PURSUIT. Resistance to the imidazolines Cyanamid under trade-marks such as PURSUIT. Resistance to the imidazolines is conferred by the gene AHAS or ALS. One skilled in the art could introduce the mutant form of AHAS present in varieties such as the Pioneer® spring canola variety, 45A71, into a Brassica plant which also carries the Rf gene for the ogura cytoplasm. Alternatively, one could introduce a modified form of the AHAS gene with a suitable promoter into a canola plant cell through any of several methods. Basically, the genes are introduced into a plant cell, such as a plant cell of this invention carrying the restorer gene for ogura cytoplasmic male sterility, and then the plant cell grown into a Brassica plant.

All publications, patents and patent applications are herein incorporated by reference in their entirety to the same extent as if each individual publication, patent or patent application was specifically and individually indicated to be incorporated by reference in its entirety.

The present invention has been described in detail and with particular reference to the preferred embodiments; however, it will be understood by one having ordinary skill in the art that changes can be made thereto without departing from the spirit and scope thereof.

REFERENCES

J. K. Daun et al, *J. Amer. Oil Chem. Soc.*, 60:1751–1754 (1983)

Delourme R., F. Eber, M. Renard. "*Breeding Double Low Restorer Lines in Radish Cytoplasmic Male Sterility of Rapeseed (Brassica napus L.)*." Proc. 9th Int. Rapeseed Conf., Cambridge Enland (1995).

Delourme R., F. Eber, M. Renard. "*Radish Cytoplasmic Male Sterility in Rapeseed: Breeding Restorer Lines with a Good Female Fertility.*" Proc 8th Int. Rapeseed Conf., Saskatoon, Canada. 1506–1510 (1991).

Delourme R., A. Bouchereau, N. Hubert, M. Renard, B. S. Landry. "*Identification of RAPD Markers Linked to a Fertility Restorer Gene for the Ogura Radish Cytoplasmic Male Sterility of Rapeseed (Brassica napus L.).*" Theor. Appl. Gener. 88: 741–748 (1994).

Delourme, R. and F. Eber. "*Linkage Between an Isozyme Marker and a Restorer Gene in Radish Cytoplasmic Male Sterility of Rapeseed (Brassica napus L.).*" Theor. Appl. Genet. 85:222–228 (1992).

International Standard ISO 9167-1:1992(E). "Rapeseed—Determination of glucosinolates content—Part 1: Method using high-performance liquid chromatography."

Paul, et al., *Theor. Appl. Genet.* 72: 706–709, (1986).

Pellan-Delourme, R., Eber, F., Renard, M. 1987. *Male fertility restoration in Brassica napus with radish cytoplasmic male sterility.* Proc. 7th Int. Rapeseed Conf., Poznan, Poland: 199–203.

Pellan-Delourme, R. and Renard, M. 1988. *Cytoplasmic male sterility in rapeseed (Brassica napus L.): Female fertility of restored rapeseed with "ogura" and cybrids cytoplasms.* Genome 30:234–238.

Pelletier G., C. Primard. "*Molecular, Phenotypic and Genetic Characterization of Mitochondrial Recombinants in Rapeseed.*" Proc. 7th Int. Rapeseed Conf., Poznau, Poland 113–118 (1987).

Rakow, G. and D. I. McGregor. "Opportunities and Problems in Modification of Levels of Rapeseed $C_{18}$ Unsaturated Fatty Acids." *J. Am. Oil Chem. Soc.* 50(10): 400–403, (1973).

Ratledge, Colin, Dawson, Peter and Rattray, James. 1984. *Biotechnology for the Oils and Fats Industry.* American Oil Chemists' Society, Champaign. 328pp Röbbelen, Gerhard. "Changes and Limitations of Breeding for Improved Polyenic Fatty Acids Content in Rapeseed." (Chapter 10) in "Biotechnology for the Oils and Fats Industry" edited by Colin Ratledge, Peter Dawson and James Rattray, American Oil Chemists' Society, (1984).

Röbbelen, G. and A. Nitsch. Genetical and Physiological Investigations on Mutants for Polyenic Fatty Acids in Rapeseed, *Brassica napus* L. *Z. Planzenzüchtg.*, 75: 93–105, (1975).

Sosulski, F., and K. Dabrowski. "Determination of Glucosinolates in Canola Meal and Protein Products by Desulfation and Capillary Gas-Liquid Chromatrography." *J. Agric. Food Chem.* 32: 1172–1175 (1984).

Stefansson, B. R. "The Development of Improved Rapeseed Cultivars." (Chapter 6) in "High and Low Erucic Acid Rapeseed Oils" edited by John K. G. Kramer, John K. G., Frank D. Sauer. and Wallace J. Pigden. Academic Press Canada, Toronto (1983).

Tsunada, S, K. Hinata, and Gomex Campo. "Brassica Crops and Wild Alleles Biology and Breeding." Japan Scientific Press, Tokyo (1980).

The seeds of the subject invention were deposited in the American Type Culture Collection (ATCC), 12301 Parklawn Drive, Rockville, Md., 20852, U.S.A.

| Seed | Accession No. | Deposit Date |
|---|---|---|
| *Brassica napus* oleifera 97SN-1650 | 97838 | Dec. 23 1996 |
| *Brassica napus* oleifera 97SN-1651 | 97839 | Dec. 23 1996 |
| *Brassica napus* oleifera 97FNW-1792-03 | 209001 | Apr. 28 1997 |
| *Brassica napus* oleifera 96FNW-1822-07 | 209002 | Apr. 28 1997 |

We claim:

1. Seed from an oilseed Brassica plant comprising a homozygous fertility restorer gene for ogura cytoplasmic male sterility, representative seed of the plant comprising a homozygous fertility restorer gene having been deposited under ATCC Accession Nos. 97838, 97839, 209001, or 209002.

2. The seed of claim 1, wherein the oilseed has a glucosinolate content of less than 30 μmol per gram.

3. The seed according to claim 2, wherein the oilseed has a glucosinolate content of less than 25 μmol per gram.

4. The seed according to claim 3, wherein the oilseed has a glucosinolate content of less than 20 μmol per gram.

5. An oilseed Brassica plant, or parts thereof, produced by growing the seed of claim 1.

6. An oilseed Brassica plant comprising a homozygous fertility restorer gene for ogura cytoplasmic male sterility, representative seed of the plant comprising a homozygous fertility restorer gene having been deposited under ATCC Accession Nos. 937838, 97839, 209001, or 209002.

7. The plant of claim 6, wherein upon pollination the plant yields oilseeds having a total glucosinolate content of not more than 30 μmol per gram.

8. The plant of claim 7, wherein upon pollination the plant yields oilseeds having a total glucosinolate content of not more than 25 μmol per gram.

9. The plant of claim 8, wherein upon pollination the plant yields oilseeds having a total glucosinolate content of not more than 20 μmol per gram.

10. The plant of claim 6, wherein upon pollination the plant yields oilseeds having an erucic acid content of no more than 2 percent by weight based upon the total fatty acid content.

11. The plant of claim 7, wherein upon pollination the plant yields oilseeds having an erucic acid content of no more than 2 percent by weight based upon the total fatty acid content.

12. The plant of claim 8, wherein upon pollination the plant yields oilseeds having an erucic acid content of no more than 2 percent by weight based upon the total fatty acid content.

13. The plant of claim 9, wherein upon pollination the plant yields oilseeds having an erucic acid content of no more than 2 percent by weight based upon the total fatty acid content.

14. An inbred oilseed Brassica plant produced using as a parent an oilseed Brassica plant comprising a homozygous fertility restorer gene for ogura cytoplasmic male sterility, representative seed of the plant comprising a homozygous fertility restorer gene having been deposited under ATCC Accession Nos. 97838, 97839, 209001, or 209002, said inbred plant comprising said homozygous fertility restorer gene.

15. The inbred plant of claim 14, wherein upon pollination the inbred plant yields oilseed having a total glucosinolate content of less than 30 μmol per gram.

16. The inbred plant of claim 15, wherein upon pollination the inbred plant yields oilseed having a total glucosinolate content of less than 25 μmol per gram.

17. The inbred plant of claim 16, wherein upon pollination the inbred plant yields oilseed having a total glucosinolate content of less than 20 μmol per gram.

18. A hybrid oilseed Brassica plant produced using as a parent an oilseed Brassica plant comprising a homozygous fertility restorer gene for ogura cytoplasmic male sterility, representative seed of the plant comprising a homozygous fertility restorer gene having been deposited under ATCC Accession Nos. 97838, 97839, 209001, or 209002, said hybrid plant comprising said fertility restorer gene.

19. The hybrid plant of claim 18, wherein upon pollination the hybrid plant yields oilseed having a total glucosinolate content of less than 30 μmol per gram.

20. The hybrid plant of claim 19, wherein upon pollination the hybrid plant yields oilseed having a total glucosinolate content of less than 25 μmol per gram.

21. The hybrid plant of claim 20, wherein upon pollination the hybrid plant yields oilseed having a total glucosinolate content of less than 20 μmol per gram.

22. A descendant plant of an oilseed Brassica plant, which oilseed Brassica plant comprises a homozygous fertility restorer gene for ogura cytoplasmic male sterility, representative seed of the oilseed plant having been deposited under ATCC Accession Nos. 97838, 97839, 209001, or 209002, wherein said descendant comprises said fertility restorer gene.

23. The descendant plant of claim 22, wherein upon pollination the descendant plant yields oilseed having a total glucosinolate content of less than 30 μmol per gram.

24. The descendant plant of claim 23, wherein upon pollination the descendant plant yields oilseed having a total glucosinolate content of less than 25 μmol per gram.

25. The descendant plant of claim 24, wherein upon pollination the descendant plant yields oilseed having a total glucosinolate content of less than 20 μmol per gram.

26. A hybrid plant produced from the descendant plant of claim 22, wherein said hybrid plant comprises said fertility restorer gene.

27. An inbred plant produced from the descendant plant of claim 22, wherein said inbred plant comprises said homozygous fertility restorer gene.

28. A part of an oilseed Brassica plant of claim 6.

29. The plant part of claim 28, wherein the part is selected from the group consisting of tissue, cells, pollen, ovule, roots, leaves, oilseeds, microspores, and vegetative parts.

30. A method for producing a hybrid oilseed Brassica plant comprising crossing the plant of claim 6 with a second oilseed Brassica plant to produce a hybrid plant.

31. The method of claim 30, wherein upon pollination the hybrid plant yields oilseed having a total glucosinolate content of less than 30 $\mu$mol per gram.

32. The method of claim 31, wherein upon pollination the hybrid plant yields oilseed having a total glucosinolate content of less than 25 $\mu$mol per gram.

33. The method of claim 32, wherein upon pollination the hybrid plant yields oilseed having a total glucosinolate content of less than 20 $\mu$mol per gram.

* * * * *